United States Patent [19]

Weatherby et al.

[11] Patent Number: 5,062,415
[45] Date of Patent: Nov. 5, 1991

[54] CERVICAL TRACTION ORTHOTIC DEVICE

[75] Inventors: John H. Weatherby, Mullica Hill, N.J.; Jack M. Potts, Danielsville, Pa.

[73] Assignee: Sttop Industries, Inc., Allentown, Pa.

[21] Appl. No.: 583,670

[22] Filed: Sep. 17, 1990

[51] Int. Cl.⁵ .............................................. A61F 5/08
[52] U.S. Cl. .................................. 128/76 R; 128/87 B
[58] Field of Search ...................... 128/75, 76 R, 84 C, 128/69, 87 B; 403/341; 606/54, 56, 59, 73, 87; 272/123

[56] References Cited

U.S. PATENT DOCUMENTS

| | | | |
|---|---|---|---|
| 867,312 | 10/1907 | Shutz | 403/341 |
| 3,022,073 | 2/1962 | Miller | 272/123 |
| 3,534,731 | 10/1970 | Muller | 128/92 |
| 4,352,585 | 10/1982 | Spalding | 403/341 X |
| 4,360,028 | 11/1982 | Barbier et al. | 128/659 |
| 4,386,603 | 6/1983 | Mayfield | 128/69 |
| 4,420,154 | 12/1983 | Ramsey et al. | 272/123 X |
| 4,444,179 | 4/1984 | Trippi | 128/75 |
| 4,620,530 | 11/1986 | Lanier et al. | 128/75 |
| 4,620,533 | 11/1986 | Mears | 128/92 |
| 4,635,930 | 1/1987 | Cormier | 272/123 |
| 4,667,660 | 5/1987 | Eingorn | 128/75 |
| 4,765,317 | 8/1988 | Eastman et al. | 128/87 B X |
| 4,807,605 | 2/1989 | Mattingly | 128/75 |
| 4,838,264 | 6/1989 | Bremer et al. | 128/303 |
| 4,934,354 | 6/1990 | Anapliotis | 128/69 X |
| 4,951,655 | 8/1990 | MacMillan et al. | 128/76 R |

FOREIGN PATENT DOCUMENTS

| | | | |
|---|---|---|---|
| 764670 | 9/1980 | U.S.S.R. | |
| 238831 | 8/1925 | United Kingdom | 272/123 |

Primary Examiner—V. Millin
Assistant Examiner—J. Doyle
Attorney, Agent, or Firm—Thomas A. Lennox

[57] ABSTRACT

A cervical traction orthotic apparatus including a carbon fiber reinforced halo ring with a horizontal shoulder extending inwardly forming a horizontal annular surface with a multiplicity of threaded inserts force-fitted in a multiplicity of horizontal circular holes with an integral stop member with a surface that engages the horizontal annular surface to prevent the insert from twisting. The apparatus also includes a support rod device to hold the halo ring in place, each rod being in two parts with complimentary mating shapes having aligned surfaces that are horizontal and vertical positioned such that the cross-section of the mated area is the same cross-section as the two support rod sections and a locking cylindrical sleeve to closely fit over the mated sections of the rod sections with a locking member interfitted through a hole a rod section to retain the locking sleeve over the mated sections of the rods.

19 Claims, 2 Drawing Sheets

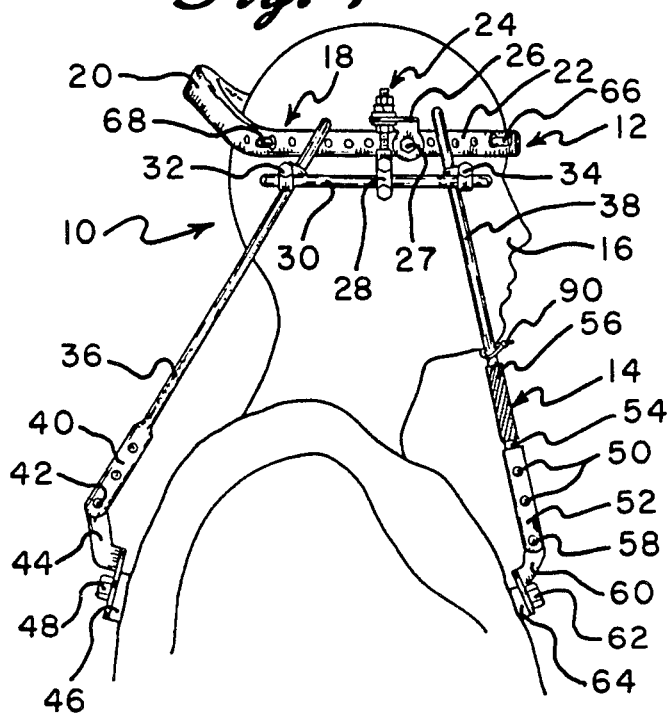
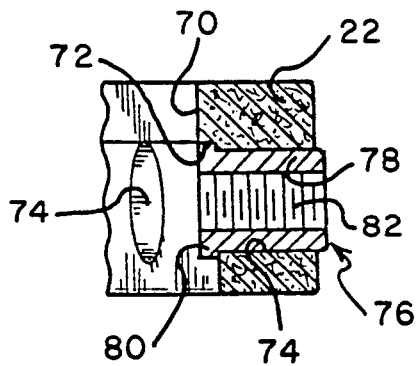
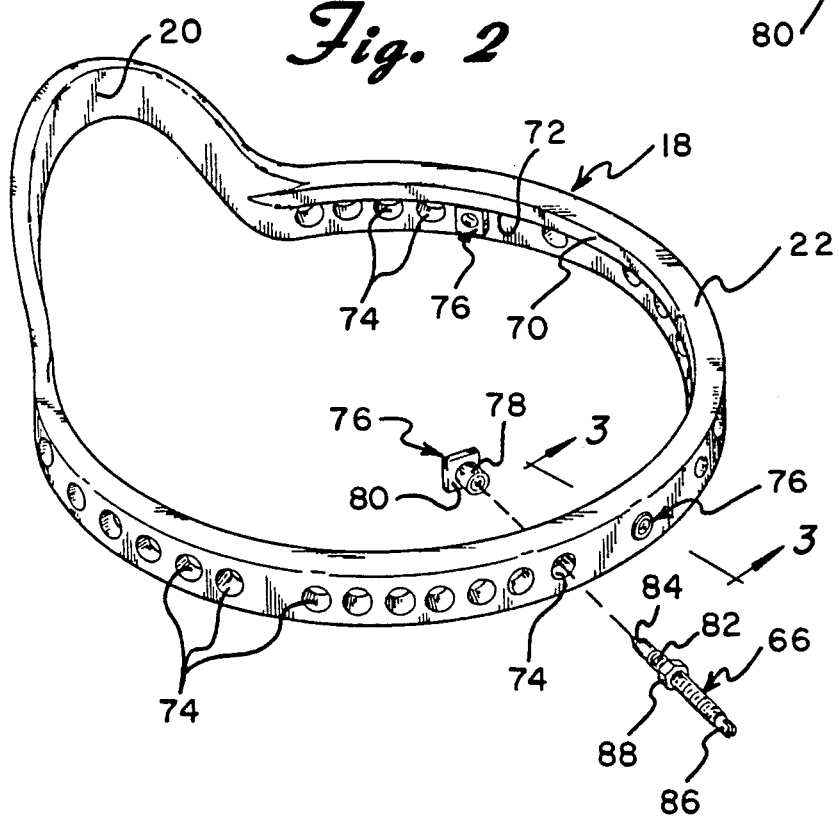

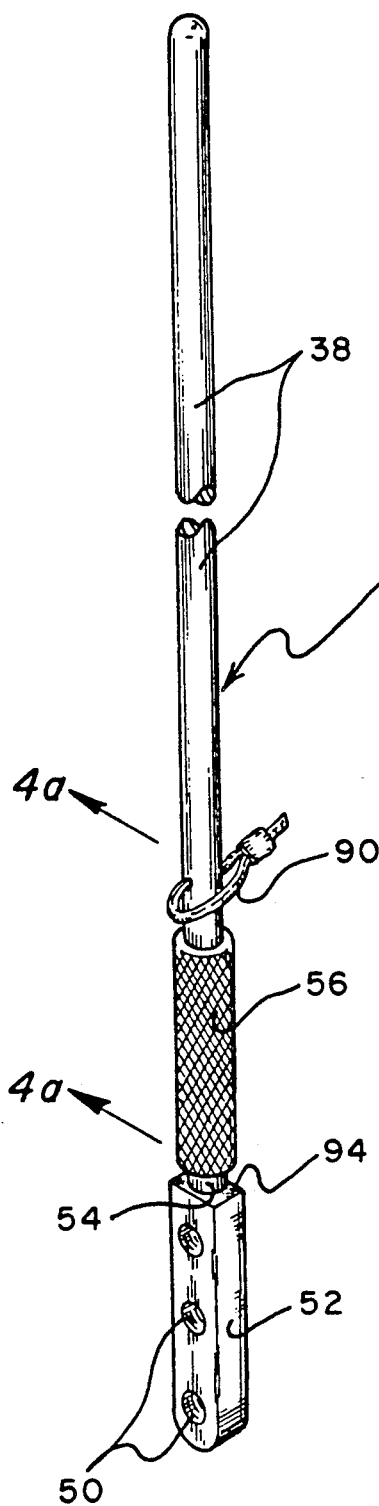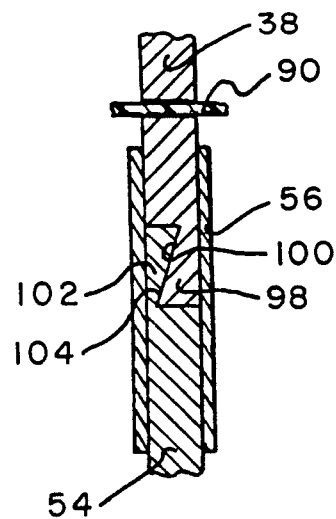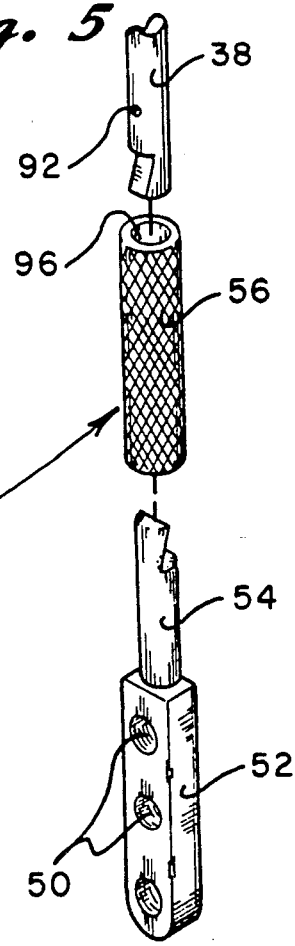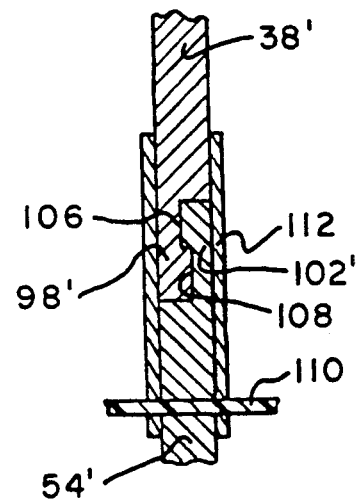

CERVICAL TRACTION ORTHOTIC DEVICE

BACKGROUND OF THE INVENTION

This invention involves a device to immobilize and stabilize the cervical vertebrae in an upright alignment, generally known as cervical traction orthosis of a patient.

Cervical traction orthotic devices have been used for some time to stabilize the cervical vertebrae, most often for patients with fractures of the cervical vertebrae. These devices generally include a semi-rigid vest constructed of polyethylene polymeric plastic formed sheet that is strapped around the patient's chest. Support rod members are structurally attached to the vest and extend upwardly to positions around the person's head. A rigid generally oval shaped ring is releasably attached to the upper ends of the support rods. The ring, generally in the form of an oval, has a raised section positioned to the rear of the patient's head with the balance of the ring being positioned generally horizontal. A multiplicity of horizontal holes are provided along the entire length of the horizontal portion of the ring. Surgical titanium threaded pins threadably engaged in the holes are adjusted and screwed through the ring to engage the skull and hold the patient's head in position.

The rings have been made of a variety of materials, stainless steel, titanium, aluminum, although the modulus of the latter material is generally too low, and, more recently, carbon fiber reinforced composite materials. An advantage of the composite material is that they do not affect the field when placed in the extremely strong magnetic field of the magnetic resonance imaging testing apparatus, generally referred to as "MRI". It is a common practice to place a patient having a fractured cervical vertebrae in an MRI apparatus. Sometimes these tests are prescribed for the fracture itself, but are also many times required because of other injuries or complications. The common stainless steel rings provide too much magnetic disturbance in the MRI scanner causing arcs, burns, and at the minimum, disruption of the testing procedures with false images. Unfortunately, problems arise with the carbon fiber reinforced composite materials including failure to maintain a stable thread and thus a firm positioning of the skull pins. The use of helicoil metal threads engaged directly into the horizontal holes of the carbon reinforced composite ring provide inconsistent results, variations in torque required to move the skull pins through the threads. If metal threads are not utilized and the threads are cut directly into the composite ring the threads are a high incidence particulate contamination source. There is a major concern of fine particulate being abraded off of the ring threads to the threads of the pin and ultimately possibly reaching the patient's skull. The very nature of the titanium skull pins are electrostatic in nature and positioned such that any particulate matter abraded or broken away from the carbon fiber reinforced rings tends to be attracted to the point of the skull pins, the very point in contact with the person's skull. Such contamination can form an ulcer and possible entry into the patient's blood stream. Since the entry of foreign materials through the skin and to the skull creates a potential for great hazard to the patient, such risks cannot be tolerated.

An additional problem with present orthotic devices involves the necessity of reaching the patient's chest for emergency procedures. For example, if the patient were to suffer a cardiac arrest or even an arrhythmia, serious harm could come to the patient if either a substantial delay were to be required to remove the device or that the entire device had to be removed in order to reach the patient's chest. As a result, it has been desirable to have at least the front support rod members to be releasably hinged to allow access to the person's chest by allowing the vest to be peeled back in order to reach the patient's chest. Unfortunately, because of the angles involved from the chest to the head ring, the hinges tend to bind and become easily twisted and permanently damaged. Loosening the bolts and detaching the front support rods is too time consuming in case of a cardiac arrest.

Prior devices described in U.S. Pat. No. 4,620,530 to LANIER ET AL as well as all of the devices described in the patents and publications cited as references in that patent, all incorporated herein by reference, fail to satisfy the above needs nor attain the objects described herein below.

SUMMARY OF THE INVENTION

It is an object of the present invention to provide a cervical traction orthotic device that utilizes a high modulus composite construction with essentially no interference in a highly concentrated magnetic resonance instrument.

It is a further object of the present invention to provide a cervical traction orthotic device utilizing a composite halo ring with threaded insert devices that allow a secure, essentially trouble-free thread attachment of the skull pins.

It is an additional object of the present invention to provide thread attachment devices which allow the threaded skull pins to engage the head with little risk from foreign substance entrainment on the threads which might reach the patient's skull.

It is an additional object of the present invention to provide female threaded inserts into a composite halo ring that offers consistent constant torque resistance from insert to insert for the skull pins to allow control of the torque pressure against the skull to be controlled within narrow tolerances.

It is a particular object of the present invention to provide a threaded insert into composite halo cervical traction devices which cannot be twisted upon threadably inserting the skull pins.

It is a further object of the present invention to provide consistent torque pressure on each skull pin threadably inserted in a composite halo ring in a cervical traction orthotic device.

It is an additional object of the present invention to provide a composite ring in a cervical traction orthotic device wherein the possibility of particulate matter reaching the head of the patient is substantially reduced, if not totally eliminated.

It is a further object of the present invention to provide a cervical traction device which utilizes complete electrical paths within the device such that current at the high voltages in the MRI apparatus merely flow around the path without interruption, arcing, or interference with the procedures.

It is a particular object of the present invention to provide a cervical traction device that insulates the patient from electrical high voltage currents present in the MRI apparatus.

An aspect of the invention is a halo ring and skull pin attachment device in a cervical traction orthotic apparatus that includes a form fitting semi-rigid vest, support rods structurally attached to and extending from the vest upwardly to a halo support ring, and connection means to adjustable and structurally attach lower ends of the support rods to the vest, and upper ends of the rods to the halo ring. The device includes the halo ring member that includes a partial oval section positionable essentially horizontally above the ears of the patient encircling the head from behind the ears around the forehead of the patient. The partial oval section includes a center, an outside surface facing outwardly from the center, and an inside surface facing inwardly toward the center. The oval ring is an integral composition of unidirectional fibers around the ring member in a reinforced composite material. The partial oval section further includes a horizontal shoulder extending inwardly from the inside surface of the partial oval section of the ring toward the center forming a horizontal annular surface, and a multiplicity of horizontal circular holes through the partial oval section opening from the outside surface to the inside surface. The device further includes a multiplicity of insert devices each of which includes a body that includes an outside shape and size to press fit into the horizontal holes and a length extending outwardly past the outside surface. Each body has a bore the length of the body opening at both ends of the body forming an inside lengthwise cylindrical surface and spiral threads on the inside surface of the bore. Each insert device also includes stop means to prevent the body from rotating in the hole that includes an integral member of the insert device located on an end of the body comprising at least one surface to abut the horizontal annular surface when the insert device is fitted into a hole.

It is preferred that the composition of the ring be carbon fiber reinforced epoxy resin. It is further preferred that the horizontal annular surface of the horizontal shoulder be about twenty-five to about sixty-five mils wide. It is also preferred that the holes be about three-eighths inch in diameter. It is further preferred that there be about eighteen to about thirty holes. It is also preferred that the horizontal shoulder extend from an upper edge of the inside surface of the partial oval section forming the horizontal annular surface on the bottom of the shoulder. It is also preferred that the stop means include a square shaped member positioned normal to the central axis of the bore. It is further preferred that the insert devices receiving the skull pins be coated with an electrically insulating coating.

Another aspect of the invention is a breakaway support rod device in a cervical traction orthotic apparatus that includes a form fitting semi-rigid vest, support rods structurally attached to and extending from the vest upwardly to a halo support ring, and connection means to adjustably and structurally attach lower ends of the support rods to the vest, and upper ends of the rods to halo ring. The device is preferably used in the two support rods positioned towards the front and attaching to the front of the vest. The device includes an upper rod section of at least one of the support rods having an upper end and a lower end, the upper end connectable to the halo support ring through the connection means. The device further includes a lower rod section one of the support rod having an upper end and a lower end, the lower end connectable to the vest through the connection means. The device also includes the lower end of the upper section and the upper end of the lower section interconnectable by complimentary mating shapes that include first mating aligned surfaces that are proximately horizontal and second aligned mating surfaces that are proximately vertical. It is preferred that when the mating shapes are interconnected the outer surface of the cross-section of the mated ends be essentially identical to the outer surface of the cross-section of both rod sections. The device further includes a locking cylindrical sleeve having an inside size and shape to closely fit over and surround the outer surface of the cross sectional shape to slide over either section and over the mated ends. The device also includes support means to hold the sleeve at a height surrounding the mated ends, and locking means to prevent inadvertent sliding of the sleeve away from surrounding the mated ends.

It is preferred that the support rods include unidirectional fibers the length of the rod member in a reinforced composite material. It is further preferred that the mating surfaces be "Z" shaped. It is also preferred that the support rods be round rods and the cylindrical sleeve be round. It is further preferred that the support means and the locking means include a first hole through the support rod, two holes through the locking sleeve aligned with the first hole, and a locking member insertable through the aligned holes. It is also preferred that the locking means include a first hole through the upper section of the support rod and a locking member insertable through the hole. It is further preferred that the support means include an upper surface of a member of the connecting means connecting the lower end of the lower end section to the vest. It is also preferred that the connection means connecting the upper ends of two upper end sections to the halo support ring include electrically conductive bolts threadably engaged into a multiplicity of electrically conducting insert devices that include a body that includes an outside shape and size to press fit into horizontal holes through the halo ring and a length extending outwardly past an outside surface of the halo ring, a bore the length of the body opening at both ends of the body forming an inside lengthwise cylindrical surface, spiral threads on the inside surface of the bore, and stop means to prevent the body from rotating in the hole. It is further preferred that the connection means connecting the lower ends of two lower end sections to the vest are electrically connected and the halo, support rods, and the connection means are all electrically conductive. It is also preferred that the connection means connecting the lower ends of two lower end sections to the vest are electrically connected and the halo, support rods, and the connection means are all electrically conductive.

BRIEF DESCRIPTION OF DRAWINGS

FIG. 1 is a left side elevational view of a cervical traction orthotic device of the present invention shown as applied to a patient.

FIG. 2 is a front and top left side perspective view of a halo ring of the present invention as illustrated in FIG. 1.

FIG. 3 is an expanded partial cross-sectional view taken along lines 3—3 of FIG. 2.

FIG. 4 is a perspective view of a support member of the present invention as illustrated in FIG. 1.

FIG. 4a is a cross-sectional view taken along lines 4a—4a of FIG. 4.

FIG. 4b is a cross-sectional view of an alternative embodiment of the present invention taken along lines 4b—4b of a modified device from that of FIG. 4.

FIG. 5 is an exploded perspective view of the support member illustrated in FIG. 4.

DESCRIPTION OF PREFERRED EMBODIMENTS

As illustrated in FIG. 1, cervical traction orthotic device 10 of the present invention is illustrated on patient 16 who is wearing a standard support vest constructed of semi-rigid polymeric plastic formed of breast and back plates suitably padded with lamb's wool or artificial lamb's wool between the patient and the polymeric plastic plates which are tightly strapped with buckle attachments around the patient's chest. Device 10 is releasably and structurally attached to the polymeric plastic plates of the vest and includes halo ring device 12 supported and held in rigid position by support member device 14. Halo ring device 12 includes carbon fiber reinforced composite ring 18 that is shaped to encircle the person's head, just above the ear line. Ring 18 includes horizontal front portion 22 which is positioned and held in an essentially horizontal position by support device 14. Ring 18 also includes elevated rear section 20 which angles upwardly from the horizontal to allow access to the person's head in the rear. Device 10 also includes right angle attachment device 24 which provides releasable and adjustable structural attachment from ring device 18 to support rods which support the ring in rigid position from the standard vest around the patient's torso. Attachment device 24 includes bracket mechanism 26 which provides adjustable and structural attachment to section 22 of ring 18. Bracket 28 provides adjustable and structural attachment between horizontal rod member 30 and bracket 26. Horizontal rod member 30 is attached by bracket 32 in an adjustable fashion to the upper portion of rear left support device 36 while bracket 34 provides structural and adjustable attachment along the length of upper section 38 of support rod device 14 which is positioned in the upper left position with regard to device 10. All the individual parts of attachment device 24 are constructed of either composite reinforced with carbon fiber, titanium or aluminum they being chosen for structural strength and electrical conductivity. Bracket 26 is adjustable in a vertical rotational plane facing forwardly with respect to ring 18 while bracket 28 is adjustable in a horizontal rotational movement with respect to bracket 26. Bracket 28 is adjustable along the length of horizontal rod 30 and rotationally with respect to the support rods. Each adjustment is able to be fixed in a set position to adjust for the head and torso size of the patient. In addition, brackets 32 and 34 are adjustable and able to be fixed in any position along the length of rod sections 36 and 38. Only one side of device 10 is shown and illustrated as the opposite, right side, is a mirror image duplication of that shown in FIG. 1. Rod device 36 includes lower section 40 which has a plurality of horizontal holes tapped through that section which is attachable by bolt 42 to bracket 44 which is releasably and structurally attached by bolt 48 to horizontal rear support member 46 of the standard vest. Member 46 provides structural support and connection to the vest as well as electrical conductivity to close the loop to the left rear counter-part of the support rod mechanism. Likewise horizontal member 64 closes the electrical loop between the front right support device 14 and the identical left front support hidden in FIG. 1. Support rod 36, is constructed of uni-directional carbon fiber reinforced composite material as are all of the individual vertical support rods including the rod of device 14 described in detail hereinbelow and attached through end attachment section 52 which extends from lower section 54 of support member device 14. Locking cylindrical aluminum tube 56 locks engaged lower end of section 38 with upper end of section 54 when device 14 is supporting ring 18. End attachment section 52 is attached at its lower end by bolt 58 threadably connecting bracket 60 which in turn is structurally and adjustably attached by bolt 62 to front left breast plate 64 of the standard vest. Front left skull pin 66 and rear left skull pin 68 are threadably engaged and extend through ring 18 to engage the skull of patient 16. There are four skull pins in total generally positioned on opposite sides of ring 18 to hold the patient's head in position.

In FIGS. 2 and 3, ring 18 is shown with threaded titanium inserts 76 to which skull pins, such as pin 66 are threadably engaged. Uncoated inserts 76 are used to attach bolts 27, right and left to ring 12. Horizontal section 22 of ring 18 is an essentially elliptically shaped member, about three quarters inch high and about three eighths inch thick. Shoulder 70 extends outwardly from the top inside edge of section 22 around the entire periphery of that section of ring 18. Shoulder 70 is an integral part of the composite molding and extends about forty-five mils away from the inside surface of section 22 forming lower horizontal surface 72 under shoulder 70. This annular inverted step surface 72 is about forty-five mils wide the width preferably being the range of about twenty-five mils to about seventy-five mils. As the width is narrowed below twenty-five mils, the step becomes too thin to structurally hold threaded insert 76 in position and a thickness greater than about seventy-five mils is unnecessary making ring section 22 either wider than necessary at the top or of insufficient thickness in the main body below. A multiplicity of holes 74 here about twenty-six of which four are used to connect through devices 76 the support rods and the balance for skull pins are drilled horizontally through the middle of section 22 around the entire periphery of that section. Four of these holes receive uncoated inserts 76 and bolts 27 which attach bracket 26 to ring 18 as shown in FIG. 1. The balance of holes 74 receive the skull pins threaded into coated inserts 76 such as pin 66 shown in FIG. 2, it being necessary to have the ability to move the skull pins from time to time during the use of the device. The "coating" applied to inserts 76 is chosen to render the surface of the inserts electrically non-conductive. The particular coating and method of application is not critical and may be enamel paint, plastic coating, anodized metal and the like. Threaded inserts 76 are press fitted into all holes 74 around the periphery for the skull pins. Holes 74 are about three-eighths inch in diameter and internally threaded cylindrical body 78 of each insert 76 is press fitted into holes 74. The term "press" is a term of the art indicating tolerances to achieve such a permanent engagement. Square locking end 80 is an integral part of insert 76 and is positioned transverse to cylindrical body 78 on one end. An edge of square locking end 80 engages lower step surface 72 with a close tolerance preventing any rotational movement of insert 76. Cylindrical body 78 is threaded lengthwise with female threads 82 to threadably engage male threads 84 on the outside of standard skull pin 66 having on one end pointed end 84 which engages the skull and opposite slotted end 86 on which controlled torque can be applied. Locking nut 88 is snugged against the outside surface of section 22 of ring 18 when skull pin 66 has been applied against the skull.

The ring and apparatus are attached to the patient using standard methods. Positioning pins with flat plastic ends are used to hold the ring in position against the patient's head over and behind the person's ears. Skull pins, four in number, are inserted into coated threaded inserts 76 from opposite directions over the eyes and behind the ears to finger tightness. The skull pins are then tightened in pairs to a specific torque, such as six to eight inch pounds. The nest and support rod apparatus is then attached to the ring utilizing all of the various adjustments as to angle and position to position the cervical portion of the spine in the correct position.

With this construction, electric conductivity and paths for current are complete around the ring, through attachment device 24, through support rod device 14, across horizontal member 64, and back up the left side counterparts of the devices back to ring 12. Key elements of threaded inserts 76 for receiving skull pins are that they are non-conductive of electricity by means of an insulating coating and cannot be twisted. With this construction, the amount of metal utilized in the structure is minimized thus reducing signal loss in the magnetic resonance field. A carbon fiber reinforced ring without uncoated threaded inserts would still be electrically conductive from the pins to the ring. Pin 66 and all other skull pins are standard 6-4 titanium alloy which satisfies the ASTM titanium implant grade material. Threaded lock inserts 76 may be constructed of aluminum alloy 6061T6 although other alloys such as alloy 2024T6, as well as other alloys, are quite satisfactory. Ring 18 is constructed of a composite material produced by winding carbon fiber impregnated with a heat curable bisphenol-A based epoxy resin around a two part mold including an open annular groove in the shape of ring 18. The impregnated fiber is wound tightly around the mold in the groove to fill the groove with the wound fiber. The mold is then placed in an oven and cured at temperatures up to about three hundred fifty degrees Farenheit according to the specifications provided by the supplier of the epoxy resin. The split mold is then separated allowing removal of ring 18.

While the shape of locking end 80 is illustrated as a square member, it should be apparent that other shapes would be satisfactory so long as they provide an edge to engage lower surface 72 of step shoulder 70. The locking end may be an oversized round disk with a cut off flat side or it may be triangular or hexagonal or of any other shape that provides a side capable of abutting against surface 72 and preventing body 78 from rotating.

In FIGS. 4 and 5, support member device 14 is shown with upper section 38 a carbon fiber reinforced composite round rod providing support for the attachment device 24 and ring 18. Locking aluminum sleeve 56 fits snugly over rod 38 but is easily slid upwardly along the length of section 38, if plastic lock tie 90 is removed from hole 92. Hole 92 is cut horizontally through section 38 above the positioning of tube 56 which is also surrounding lower section 54 of the support rod and rests on shoulder 94 of end attachment section 52. The use of carbon fiber reinforced composite material for all the support rods provide a strong stable support with electrical conductivity. As shown in FIG. 5 and the cross-sectional view of FIG. 4a, locking tube 56 is resting on shoulder 94 and keeps the interlocked ends of sections 38 and 54 in an interlocked position. In the case of emergency, plastic lock tie 90 is easily snipped with a pair of scissors or a knife and locking sleeve 56 is slid upwardly until it is entirely on upper section 38 allowing the engaged ends of rod sections 38 and 54 to essentially fall apart. Sleeve 56 has lengthwise bore 96 which slidably interfits over sections 38 and 54. As shown in FIG. 4a, lower end 98 terminates in "Z" cut 100 while upper end 102 of section 54 terminates in a complimentary interlocking and mating "Z" cut 104 such that when the ends are mated together, they form a continuous round rod shape, which when held in position by locking sleeve 56, is essentially as structurally rigid and strong as the rod itself. As will be apparent, other interlocking shapes of the ends of the rods will also perform satisfactorily so long as when mated a round rod is formed and the interlocked shape forms a rigid structure. In FIG. 4b, lower end 98' of section 38' is cut in interlocking "S" shape to engage and interlock with complimentary "S" shape cut 108 in end section 102' of lower section 54'. The "S" shape surface 106 includes a horizontal cut to terminate end section 38' with a cut vertically lengthwise through end section 98', followed by a reverse horizontal cut, followed by a vertical lengthwise cut continuing in the same direction as the first lengthwise cut, but in a different plane followed by a final reverse horizontal cut to complete the "S" shape. An upside down mirror image surface 108 is placed in end section 102' of a complimentary size and shape to interlock and form a continuous circular rod with locking tube 112 in place. Support for and the locking of to prevent sleeve 56 from moving away from the position surrounding the interlocked end surfaces is provided by lock tie 110, which in this embodiment passes through aligned horizontal holes through tube 112 and rod section 54'. The quick access, breakaway nature of support member device 14 allows defibrillation or heart massage of the patient by removal of the front one half of the vest to reach the left side of the chest.

While this invention has been described with reference to the specific embodiments disclosed herein, it is not confined to the details set forth and the patent is intended to include modifications and changes which may come within and extend from the following claims.

We claim:

1. A halo ring, scull pin attachment, and rod attachment device for use in cervical traction orthotic apparatus comprising a form fitting semirigid vest, support rods structurally attached to and extending from the vest upwardly to the halo support ring, first connection means to adjustably and structurally attach lower ends of the support rods to the vest, and second connection means to adjustably and structurally attach upper ends of the rods to the halo ring, the device comprising:
    (a) a halo ring member comprising:
        (i) a partial oval section positionable essentially horizontally above the ears of the patient encircling the head from behind the ears around the forehead of the patient comprising a center, an outside surface facing outwardly from the center, and an inside surface facing inwardly toward the center.
        (ii) an integral composition of unidirectional fibers around the ring member in a reinforced composite material, (iii) a horizontal shoulder extending inwardly from the inside surface of the partial oval section of the ring toward the center forming a horizontal annular surface, and (iv) a multiplicity of horizontal circular holes through the partial oval section opening from the outside surface to the inside surface, and (b) a multiplicity of insert devices comprising:
  (i) a body comprising an outside shape and size to press fit into the horizontal holes and a length extending outwardly past the outside surface,
  (ii) a bore the length of the body opening at both ends of the body forming an inside lengthwise cylindrical surface,
  (iii) spiral threads on the inside surface of the bore, and
  (iv) stop means to prevent the body from rotating in the hole comprising an integral member of the insert device located on an end of the body comprising at least one surface to abut the horizontal annular surface when the insert device is fitted into a hole.

2. The device of claim 1 wherein composition of the ring is carbon fiber reinforced epoxy resin.

3. The device of claim 1 wherein the horizontal annular surface of the horizontal shoulder is about 25 to about 65 mils wide.

4. The device of claim 1 wherein the holes are about three eighths inch in diameter.

5. The device of claim 1 wherein there are about eighteen to about thirty holes.

6. The device of claim 1 wherein the horizontal shoulder extends from an upper edge of the inside surface of the partial oval section forming the horizontal annular surface on the bottom of the shoulder.

7. The device of claim 1 wherein the stop means comprises a square shaped member positioned normal to the central axis of the bore.

8. The device of claim 1 wherein a plurality of the insert devices comprise an electrically insulating coating.

9. A breakaway support rod device comprising a plurality of support rods for use in a cervical traction orthotic apparatus comprising a form fitting semirigid vest, a halo support ring, first connection means to adjustably and structurally attach lower ends of the support rods to the vest, and second connection means to adjustably and structurally attach upper ends of the rods to halo ring, the device comprising:

(a) an upper rod section of one of the support rods having an upper end and a lower end, the upper end connectable to the halo support ring through the second connection means, (b) a lower rod section of one of the support rods having an upper end and a lower end, the lower end connectable to the vest through the first connection means, (c) the lower end of the upper section and the upper end of the lower section interconnectable by complimentary mating shapes comprising first mating aligned surfaces that are proximately horizontal and second aligned mating surfaces that are proximately vertical, wherein when the mating shapes are interconnected the outer surface of a transverse cross-section of the mated ends is essentially identical to the outer surface of the cross-section of both rod sections, (d) a locking cylindrical sleeve having an inside size and shape to closely fit over and surround the outer surface of the cross-sectional shape to slide over either section and over the mated ends, (e) support means to hold the sleeve at a height surrounding the mated ends, and (f) locking means to prevent inadvertant sliding of the sleeve away from surrounding the mated ends.

10. The device of claim 9 wherein the support rods comprise unidirectional fibers the length of the rod member in a reinforced composite material.

11. The device of claim 9 wherein the mating surfaces are "Z" shaped.

12. The device of claim 9 wherein the support rods are round rods and the cylindrical sleeve is round.

13. The device of claim 9 wherein the support means and the locking means comprise a first hole through the support rod, two holes through the locking sleeve aligned with the first hole, and a locking member insertable through the aligned holes.

14. The device of claim 9 wherein the locking means comprises a first hole through the upper section of the support rod and a locking member insertable through the hole.

15. The device of claim 9 wherein the support means comprises an upper surface of a member of the first connecting means connecting the lower end of the lower end section to the vest.

16. The device of claim 9 wherein the first connection means connecting the upper ends of two upper end sections to the halo support ring comprise electrically conductive bolts threadably engaged into a multiplicity of electrically conductive insert devices comprising:
  (i) a body comprising an outside shape and size to press fit into horizontal holes through the halo ring and a length extending outwardly past an outside surface of the halo ring,
  (ii) a bore the length of the body opening at both ends of the body forming an inside lengthwise cylindrical surface,
  (iii) spiral threads on the inside surface of the bore, and
  (iv) stop means to prevent the body from rotating in the hole.

17. The device of claim 16 wherein the second connection means connecting the lower ends of two lower end sections to the vest are electrically connected and the halo, support rods, and the connection means are all electrically conductive.

18. The device of claim 9 wherein the second connection means connecting the lower ends of two lower end sections to the vest are electrically connected and the halo, support rods, and the connection means are all electrically conductive.

19. A cervical traction orthotic apparatus comprising a form fitting semirigid vest, support rods structurally attached to an extending from the vest upwardly to a halo support ring, first connection means to adjustably and structurally attach lower ends of the support rods to the vest, and second connection means to adjustably and structurally attach upper ends of the rods to the halo ring, wherein:

(a) the halo ring comprises a halo ring member comprising:
  (i) a partial oval section positionable essentially horizontally above the ears of the patient encircling the head from behind the ears around the forehead of the patient comprising a center, an outside surface facing outwardly from the center, and an inside surface facing inwardly toward the center,
(ii) an integral composition of unidirectional fibers around the ring member in a reinforced composite material,
(iii) a horizontal shoulder extending inwardly from the inside surface of the partial oval section of the ring toward the center forming a horizontal annular surface, and
(iv) a multiplicity of horizontal circular holes through the partial oval section opening from the outside surface to the inside surface, (b) the apparatus further comprises a multiplicity of insert devices each comprising:
(i) a body comprising an outside shape and size to press fit into the horizontal holes and a length extending outwardly past the outside surface,
(ii) a bore the length of the body opening at both ends of the body forming an inside lengthwise cylindrical surface,
(iii) spiral threads on the inside surface of the bore, and
(iv) stop means to prevent the body from rotating in the hole comprising an integral member of the insert device located on an end of the body comprising at least one surface to abut the horizontal annular surface when the insert device is fitted into a hole, (c) the support rods comprise a pair of the support rods connecting to the front of the vest, each of said support rods of the pair comprising:
(i) an upper rod section having an upper end and a lower end, the upper end connectable to the halo support ring through the second connection means,
(ii) a lower rod section having an upper end and a lower end, the lower end connectable to the vest through the first connection means,
(iii) the lower end of the upper section and the upper end of the lower section interconnectable by complimentary mating shapes comprising first mating aligned surfaces that are proximately horizontal and second aligned mating surfaces that are proximately vertical, wherein when the mating shapes are interconnected the outer surface of the cross-section of the mated ends is essentially identical to the outer surface of the cross-section of both rod sections, and (d) the apparatus further comprises:
(i) a locking cylindrical sleeve having an inside size and shape to closely fit over and surround the outer surface of the cross-sectional shape to slide over either section and over the mated ends,
(ii) support means to hold the sleeve at a height surrounding the mated ends, and
(iii) locking means to prevent inadvertant sliding of the sleeve away from surrounding the mated ends.

* * * * *